US010159424B2

(12) United States Patent
Greiser et al.

(10) Patent No.: US 10,159,424 B2
(45) Date of Patent: Dec. 25, 2018

(54) METHOD AND APPARATUS FOR GENERATING MEDICAL IMAGE DATA RECORDS

(71) Applicant: Siemens Aktiengesellschaft, Munich (DE)

(72) Inventors: Andreas Greiser, Erlangen (DE); Peter Speier, Erlangen (DE); Aurelien Stalder, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 598 days.

(21) Appl. No.: 14/723,817

(22) Filed: May 28, 2015

(65) Prior Publication Data
US 2015/0342496 A1    Dec. 3, 2015

(30) Foreign Application Priority Data
May 28, 2014    (DE) .................. 10 2014 210 218

(51) Int. Cl.
*A61B 5/055*    (2006.01)
*A61B 5/00*    (2006.01)
*A61B 5/145*    (2006.01)
*G01R 33/20*    (2006.01)
*G01R 33/56*    (2006.01)
(Continued)

(52) U.S. Cl.
CPC .......... *A61B 5/055* (2013.01); *A61B 5/02055* (2013.01); *A61B 5/14546* (2013.01); *A61B 5/7278* (2013.01); *A61B 5/742* (2013.01); *G01R 33/20* (2013.01); *G01R 33/54* (2013.01); *G01R 33/5608* (2013.01); *A61B 2576/00* (2013.01)

(58) Field of Classification Search
CPC ............ A61B 2576/00; A61B 5/02055; A61B 5/055; A61B 5/14546; A61B 5/7278; A61B 5/742; A61B 5/145; G01R 33/20; G01R 33/54; G01R 33/5608
See application file for complete search history.

(56) References Cited

U.S. PATENT DOCUMENTS 6,377,834 B1 *  4/2002  Zhou .................. A61B 5/055
                                                324/315
6,768,917 B1 *  7/2004  Van Vaals ........... A61B 5/055
                                                324/315
(Continued)

OTHER PUBLICATIONS

Kellman et al., "Extracellular volume fraction mapping in the myocardium, part 1: evaluation of an automated method," Journal of Cardiovascular Magnetic Resonance, 1463, pp. 1-11 (2012).
(Continued)

*Primary Examiner* — Ruth S Smith
(74) *Attorney, Agent, or Firm* — Schiff Hardin LLP

(57) ABSTRACT

In a method and medical imaging apparatus, for generating medical image data records, raw data of the examination object are acquired by operation of a medical imaging scanner, a reconstruction algorithm issued for reconstructing a medical image data record on the basis of raw data and of a value of a physiological parameter. At least two medical image data records are created by applying the reconstruction algorithm at least twice to the acquired raw data using a different virtual value of the physiological parameter each time. The at least two medical image data records are provided from the reconstruction computer.

9 Claims, 2 Drawing Sheets

(51) Int. Cl.
  *G01R 33/54*  (2006.01)
  *A61B 5/0205*  (2006.01)

(56) References Cited

U.S. PATENT DOCUMENTS

| | | | | |
|---|---|---|---|---|
| 7,542,793 | B2* | 6/2009 | Wu | G01R 33/4804 |
| | | | | 324/300 |
| 2014/0005523 | A1* | 1/2014 | Kohler | A61B 5/055 |
| | | | | 600/411 |
| 2014/0303484 | A1* | 10/2014 | Krishnakumar | A61N 7/02 |
| | | | | 600/411 |
| 2016/0292854 | A1* | 10/2016 | Beck | A61B 5/055 |

OTHER PUBLICATIONS

Kellman et al., "Extracellular volume fraction mapping in the myocardium, part 2: initial clinical experience," Journal of Cardiovascular Magnetic Resonance, 1464, pp. 1-8 (2012).

* cited by examiner

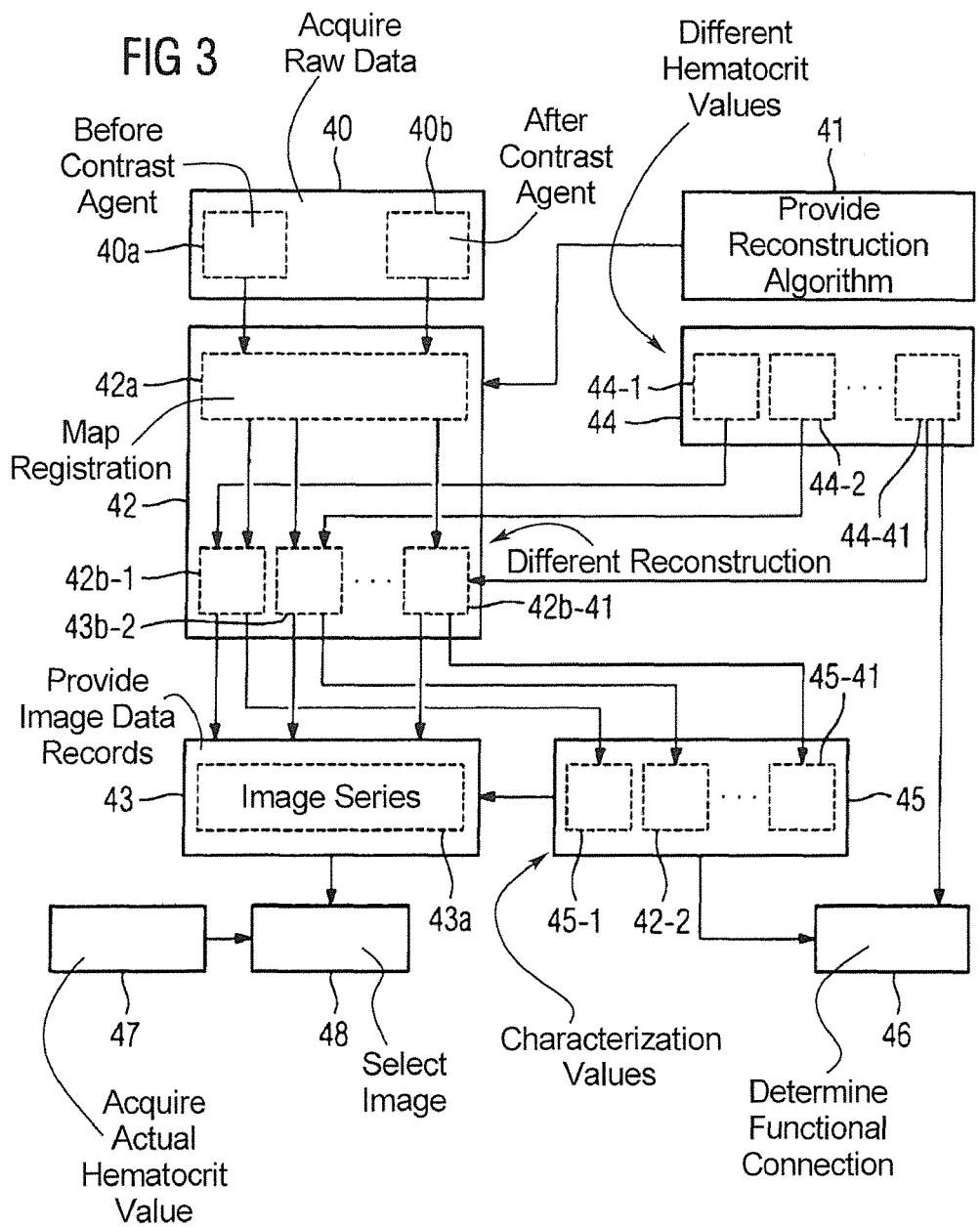

METHOD AND APPARATUS FOR GENERATING MEDICAL IMAGE DATA RECORDS

BACKGROUND OF THE INVENTION

Field of the Invention

The invention relates to a method for generating medical image data records and a medical imaging device.

Description of the Prior Art

Medical imaging devices can be used to acquire raw data from an examination object, for example a patient. This raw data can then be further processed to create a medical image data record. The medical image data record is in this case typically reconstructed from the raw data using a reconstruction algorithm. The medical image data record can then, for example, provide a specialist with insightful information about anatomy or physiology of the patient.

For the reconstruction of the medical image data record from the raw data, it may be necessary for a value of a physiological parameter of the patient to be known. The reconstruction of the medical image data record can then typically be performed only by entering a particular value of the physiological parameter into the computer that performs the reconstruction algorithm.

SUMMARY OF THE INVENTION

An object of the invention is to provide a method for improved generation of medical image data records.

In accordance with the invention, a method for generating medical image data records of an examination object on the basis of raw data, includes the following steps.

Raw data of the examination object are acquired by operation of a medical imaging device.

A computer is provided with a reconstruction algorithm for reconstructing a medical image data record on the basis of raw data and of a value of a physiological parameter.

The computer reconstructs at least two medical image data records by applying the reconstruction algorithm at least twice to the acquired raw data using a different virtual value of the physiological parameter each time.

The at least two medical image data records are provided from the computer in electronic form as data files.

The examination object can be a patient, a phantom or a training person (volunteer). The raw data are typically not provided for display on a display unit. In contrast, the at least two medical image data records are provided for display on a display unit and, for example, can be viewed and assessed by a specialist. The provision of the at least two medical image data records can thus involve a display of the at least two medical image data records on a display unit. The provision of the at least two medical image data records can also comprise storing the at least two medical image data records in a memory unit, for example a database.

The provision of the reconstruction algorithm for reconstructing a medical image data record on the basis of raw data can include selection of a suitable reconstruction algorithm. The reconstruction algorithm can have a number of reconstruction steps that are successively applied to the raw data. The provision of the reconstruction algorithm can thus be a provision of the reconstruction steps. For example, the calculation rules of the reconstruction steps can be saved in a database. The provision of the reconstruction steps can then include loading the calculation rules from the database. The reconstruction algorithm thus represents a process that uses the raw data as input parameters and that produces a medical image data record as the result.

The physiological parameter describes a physiological state of an examination object. Physiological parameters can be, for example, blood pressure, cardiac rate, oxygen saturation, temperature, or a blood parameter such as a hematocrit value. Other physiological parameters that appear expedient to those skilled in the art are also conceivable. The physiological parameter is typically specific for the respective examination object. The physiological parameter has a value that is typically specified in a unit customarily used for the physiological parameter. Thus, for example, the blood pressure is specified in mm Hg, the hematocrit value as a percentage, etc. It is also conceivable for a value, which may have a different unit and which is derived from the value of the physiological parameter, to be used for the reconstruction algorithm. The value of the physiological parameter is used as an input parameter in the reconstruction algorithm, together with the raw data. Thus different medical image data records can be produced from a single raw data record for different values of the physiological parameter.

The process according to the invention provides for multiple medical image data records to be created from the raw data. The multiple medical image data records are created from a single raw data record. This is achieved in accordance with the invention by the same reconstruction algorithm being applied at least twice to the raw data, the reconstruction algorithm being based on a different virtual value of the physiological parameter for each repetition. The at least two medical image data records thus can represent essentially the same anatomical structures of the examination object. The at least two medical image data records typically also have the same field of view. The at least two medical image data records, however, typically will have different image values of pixels or voxels because of the different physiological parameters on which the reconstruction of the at least two medical image data records is based.

The reconstruction algorithm is based on different virtual values of the physiological parameter for the reconstruction of the at least two medical image data records. The values are virtual because they have typically not yet been measured from the examination object. Thus the virtual values assumed for the reconstruction of the at least two medical image data records may possibly not correspond to the actual value of the physiological parameter of the examination object that exists when the raw data are acquired. Rather, virtual or artificial values are assumed for the physiological parameter. The virtual values can be stored in a database. The virtual values can be multiple values of the physiological parameter in a typical value range of the physiological parameter.

Thus the inventive procedure has the advantage that medical image data records are already reconstructed from the raw data and are provided, even though the actual value of the physiological parameter of the examination object may not yet have been measured and/or is not yet available. Thus the medical image data records can already be made available to a specialist before completion of the determination of the actual value of the physiological parameter of the examination object. If the actual measured value of the physiological parameter of the examination is eventually present, that medical image data record of the at least two medical image data records can be selected which was reconstructed using the value of the physiological parameter which is closest to the actual measured value. This selection can take place automatically or by a user. In particular, it is not necessary to reconstruct the medical image data again from the raw data using the actual measured value of the physiological parameter. Thus the work sequences in a medical facility can be speeded up. Furthermore, a relationship between different virtual values of the physiological parameter and of an image content of the at least two medical image data records may also advantageously be illustrated particularly vividly, as shown in one of the following sections.

In an embodiment, the reconstruction algorithm includes further processing of the raw data by a computational operation, with the value of the physiological parameter being used as a variable in the computational operation. In particular, the virtual value of the physiological parameter is used as a variable in the computational operation. The further processing of the raw data by the computational operation may also represent only one reconstruction step of the reconstruction algorithm. The reconstruction algorithm can also include further reconstruction steps that are independent of the value of the physiological parameter. The further reconstruction steps are then advantageously stored upstream of the computational operation with the physiological parameter. Thus computational time can be saved, since the reconstruction steps independent of the value of the physiological parameter have to be performed just once.

In another embodiment, the at least two medical image data records are provided together with the virtual values of the physiological parameter used during the reconstruction of the at least two medical image data records. The medical image data records are thus provided with the associated values of the physiological parameter. The associated value of the physiological parameter is here in particular that value of the physiological parameter which was used for the reconstruction of the medical image data record. The associated value of the physiological parameter can be saved in a database together with the medical image data record. The associated value of the physiological parameter can be displayed together with the medical image data record. Thus the associated values of the physiological parameter can be provided particularly easily to a specialist who is looking at the medical image data records. Thus the specialist can assess the medical image data records particularly easily.

In another embodiment, the at least two medical image data records are provided in the form of a series of images. A series of images can be a simultaneous display of the at least two medical image data records. A series of images can also be a display of a sequence of the at least two image data records. The display in the form of a series of images can provide a particularly transparent overview of the at least two medical image data records. It is possible for a particularly intuitive selection of a medical image data record in the series of images to take place by an operating element designed in the form of a slide control. The slide control can in this case change the virtual values of the physiological parameter and select the associated medical image data records in the series of images for display. Thus, for example, the associated medical image data record can be selected from the series of images particularly easily after the actual physiological parameter has been captured.

In a further embodiment, the actual physiological parameter of the examination object are acquired after the at least two medical image data records of the examination object have been created. The actual value of the physiological parameter of the examination object is not available until after the medical image data records have been created. The measurement of the physiological parameter can take place before or after the raw data are acquired, but advantageously very close to the time when the raw data are acquired. The evaluation of the measurement of the physiological parameter is then in particular not completed until after the at least two medical image data records have been created. Thus it is advantageous to create multiple medical image data records using different virtual values of the physiological parameter, since the actual value of the physiological parameter is not yet known when the medical image data records are created.

One embodiment provides for an image area of the at least two medical image data records to be determined, and for a characterization value across the image area to be determined for each of the at least two medical image data records which characterizes an image content of the image area of the at least two medical image data records, with the at least two medical image data records being provided together with the associated characterization value. The characterization value can be a feature of the image area of the medical image data record. The characterization value can characterize a distribution of signal values of the image area. Thus the characterization value can for example be a mean signal value of the image area and/or a mean signal-to-noise ratio of the image area and/or a variance value of the signal values of the image area and/or a maximum signal value of the image area. Other characterization values that appear expedient to those skilled in the art are conceivable. The image area can be determined automatically, for example by segmentation. The image area can also be established manually, in particular in the form of a region of interest (ROI) or a volume of interest (VOI). The image area advantageously has the same extent and position for all medical image data records, so that the characterization value is comparable for all medical image data records. The provision of the characterization value can in turn be a display of the characterization value, in particular combined with a display of the associated medical image data record. The provision of the characterization value can also comprise storage of the characterization value. The characterization value advantageously represents a particularly informative description of the respective image content of the medical image data records.

In another embodiment, a functional connection between the characterization value and the value of the physiological parameter is determined and the functional connection is displayed in a diagram display. Thus the characterization value can be displayed as a function of the value of the physiological parameter, which is used as the basis for creating the medical image data record associated with the characterization value. The functional connection can be displayed in a graphical display, for example in the form of a result curve. Alternatively or additionally the functional connection can be displayed in a table. Thus the functional connection between characterization value and virtual value of the physiological parameter can be displayed particularly informatively and transparently. Those skilled in the art can thus establish with particular ease what influence different values of the physiological parameter have on the characterization value.

In another embodiment, the physiological parameter is a laboratory value of the examination object. The determination of laboratory values often takes longer, so that the laboratory value of the examination is frequently not available until after the raw data has been captured or until after the medical image data records have been created. Thus it makes sense initially to create the at least two medical image data records first on the basis of virtual values of the physiological parameter. When the measured laboratory value is eventually available, the appropriate medical image data record can be selected.

In another embodiment, the physiological parameter is a hematocrit value of the examination object. This embodiment can be used particularly advantageously with the embodiments mentioned in the following two sections.

In one embodiment, the raw data comprises a T1 map of the examination object before contrast medium is administered and a T1 map of the examination object after contrast medium is administered. This embodiment can be used particularly advantageously with the embodiment mentioned in the previous section and the embodiment mentioned in the following section.

In one embodiment, the at least two medical image data records comprise a display of a spatially resolved distribution of an extracellular volume of the examination object. This embodiment can be used particularly advantageously with the embodiments mentioned in the previous two sections.

Thus raw data from the patient's heart can be acquired by operation of a magnetic resonance scanner. For example, T1 relaxation times of the heart can be determined before and after contrast medium is administered. These T1 relaxation times can then be determined quantitatively and output on a spatially resolved basis as a T1 map in each case. The T1 relaxation time, also called the spin lattice relaxation time, is the time which the longitudinal magnetization requires in order to return from the state of equilibrium back to approx. 63 percent of its initial value after an excitation.

The T1 values before and after contrast medium is administered enable a myocardial extracellular volume (ECV) to be estimated. This parameter is for example particularly advantageously suitable for performing a fibrosis quantification of cardiac muscle fibers. Thus the T1 maps can be reconstructed before and after contrast medium is administered to produce a spatially resolved display of the myocardial extracellular volume, known as an ECV map. However, for this reconstruction it is necessary to know a physiological parameter of the patient, namely the hematocrit value of the patient. The hematocrit value designates the proportion of erythrocytes to the volume of the blood or approximately the proportion of the cell volume to the blood volume. Since this hematocrit value is often not available as a laboratory value until after the raw data has been captured, the inventive procedure is particularly advantageous, since different ECV maps can initially be created on the basis of virtual hematocrit values.

Furthermore, the invention encompasses a medical imaging apparatus that has a raw data acquisition unit (scanner), a reconstruction computer and a display monitor, wherein the raw data acquisition unit, the reconstruction computer and the display monitor are designed to perform the method as described above. Thus the medical imaging apparatus is designed to perform a method for generating medical image data records of an examination object on the basis of raw data.

The raw data acquisition unit is designed to acquire raw data of the examination object. The reconstruction computer is designed to provide a reconstruction algorithm for reconstructing a medical image data record on the basis of raw data and of a value of a physiological parameter. Furthermore, the reconstruction computer is designed to reconstruct at least two medical image data records by applying the reconstruction algorithm at least twice to the captured raw data using a different virtual value of the physiological parameter each time. The display monitor is designed to provide the at least two medical image data records.

The advantages of the inventive medical imaging apparatus essentially correspond to the advantages of the inventive method, which are explained above in detail. Features, advantages or alternative embodiments mentioned herein apply equally to the other claimed subject matter and vice versa. The corresponding functional features of the method are configured by suitable modules, in particular hardware modules.

BRIEF DESCRIPTION OF THE DRAWINGS

FIG. 3 is a flowchart of a second embodiment of an inventive method.

DESCRIPTION OF THE PREFERRED EMBODIMENTS

Figure 1:
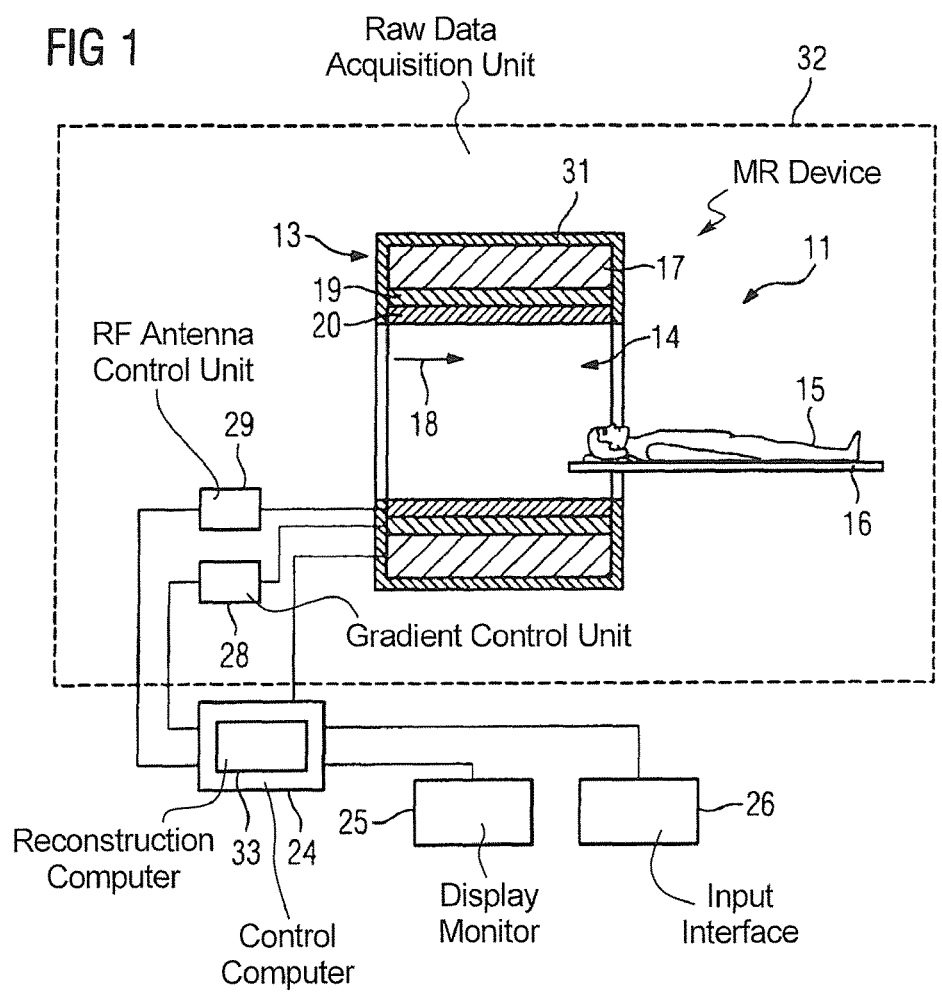
FIG. 1 schematically illustrates an inventive medical imaging device for performing the inventive method

FIG. 1 is a schematic illustration of an inventive medical imaging apparatus 11 for performing the inventive method. The medical imaging device 11 may be a magnetic resonance device, a single-photon emission computed tomography device (SPECT device), a positron emission tomography device (PET device), a computed tomography system, an ultrasound device, an X-ray device or a C-arm device. Combined medical imaging 11 are also possible, formed by any combination of several of the cited imaging modalities.

For example, the medical imaging device 11 shown in FIG. 1 is a magnetic resonance device 11. The magnetic resonance device 11 has a scanner formed by a magnet unit 13 with a basic field magnet 17 for generating a strong and constant basic magnetic field 18. Furthermore, the magnetic resonance device 11 has a cylindrical patient receiving region 14 for accommodating a patient 15. The patient receiving region 14 is cylindrically enclosed in a peripheral direction by the magnet unit 13. The patient 15 can be moved by a patient support 16 of the magnetic resonance apparatus 11 into the patient receiving region 14. To this end the patient support 16 has a bed, which is disposed in a movable manner within the magnetic resonance device 11. The magnet unit 13 is screened toward the outside by a housing covering 31.

The magnet unit 13 also has a gradient coil arrangement 19 for generating magnetic field gradients that are used for spatial encoding during imaging. The gradient coil arrangement 19 is controlled by a gradient control unit 28. Furthermore, the magnet unit 13 has a radio-frequency (RF) antenna 20 that, in the case shown, is configured as a body coil integrated into the magnetic resonance apparatus 10, and a radio-frequency antenna control unit 29 for excitation of a polarization which is created in the basic magnetic field 18 generated by the main magnet 17. The radio-frequency antenna 20 is controlled by the radio-frequency antenna control unit 29 and radiates radio-frequency magnetic resonance sequences into an examination space that is substantially formed by the patient receiving region 14. The radio-frequency antenna unit 20 is further designed to receive magnetic resonance signals, in particular from the patient 15.

For controlling the main magnet 17, the gradient control unit 28 and the radio-frequency antenna control unit 29, the magnetic resonance device 11 has a control computer 24.

The computing unit 24 is used for central control of the magnetic resonance apparatus 11, such as performing a predetermined imaging gradient echo sequence for example. Control information such as, for example, imaging parameters and reconstructed magnetic resonance images can be displayed for a user on a display monitor 25, for example on at least one monitor of the magnetic resonance device 11. Furthermore, the magnetic resonance device 11 has an input interface 26, via which information and/or parameters can be entered by a user during a measurement procedure. The control computer 24 can include the gradient control unit 28 and/or the radio-frequency antenna control unit 29 and/or the display unit 25 and/or the input interface 26.

The magnetic resonance device 11 further forms a raw data acquisition unit 32 (scanner). The raw data acquisition unit 32 (scanner) is formed by the magnet unit 13 together with the radio-frequency antenna control unit 29 and the gradient control unit 28. The control computer 24 further has a reconstruction computer 33. The magnetic resonance device 11 is thus designed, together with the raw data acquisition unit 32, the display monitor 25 and the reconstruction computer 33, to perform the inventive method.

The magnetic resonance device 11 that is shown can have further components that magnetic resonance devices 11 typically have. The general method of functioning of a magnetic resonance device 11 is known to those skilled in the art, so that a detailed description of the further components is not necessary.

Figure 2:
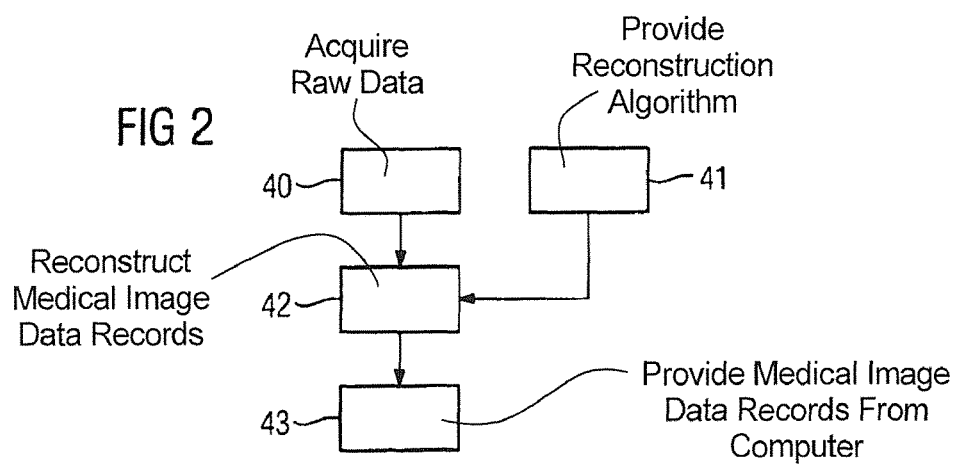
FIG. 2 is a flowchart of a first embodiment of the inventive method.

FIG. 2 is a flowchart of a first embodiment of an inventive method for generating medical image data records of an examination object on the basis of raw data.

In a first method step 40 raw data of the examination object are acquired by the medical imaging device 11. With reference to FIG. 1, it is possible for the raw data to be acquired by operation of the raw data acquisition unit 32 of the magnetic resonance device 11.

In a further method step 41, a reconstruction algorithm is provided by the reconstruction computer 33 of the medical imaging device 11 for the creation of a medical image data record on the basis of raw data and a value of a physiological parameter.

In a further method step 42, the reconstruction computer 33 creates at least two medical image data records by applying the reconstruction method at least twice to the captured raw data using a different virtual value of the physiological parameter each time.

In a further method step 43, the at least two medical image data records are provided, for example on a display monitor 25. The provision can also be storage of the at least two medical image data records in a database.

FIG. 3 shows a flowchart of a second embodiment of a method according to the invention. The following description is essentially restricted to the differences from the exemplary embodiment in FIG. 2 wherein, with regard to method steps which remain the same, reference can be made to the description of the exemplary embodiment in FIG. 2. In principle, the same method steps are identified with the same reference characters.

The second embodiment of the inventive method shown in FIG. 3 includes method steps 40,41,42,43 of the first embodiment of the inventive method as shown in FIG. 2. The second embodiment of the inventive method shown in FIG. 3 additionally has further method steps and substeps. Also conceivable is an alternative method sequence to that of FIG. 3 which has only part of the additional method steps and/or substeps represented in FIG. 2. Naturally, an alternative method sequence to that of FIG. 3 can also have additional method steps and/or substeps.

In FIG. 3 will be described using the example of the medical image data records being a representation of a spatially resolved distribution of an extracellular volume of the examination object, known as an ECV map. The physiological parameter is then a hematocrit value of the examination object, which is necessary for calculating the extracellular volume. Obviously other applications of the inventive method that appear expedient to the person skilled in the art are also conceivable. FIG. 3 shows only one possible advantageous way in which the inventive method can be performed.

In the method step 40, namely the acquisition of the raw data of the examination object, which in the present case is a patient 15, a T1 map of the examination object is captured before contrast medium is administered in a first substep 40a and a T1 map of the examination object is captured after contrast medium is administered in a second substep 40b by means of the raw data capture unit 32. The two T1 maps thus represent the raw data captured in the further method step 40.

In the further method step 41, the provision of the reconstruction method, the reconstruction computer 33 provides a reconstruction algorithm for reconstructing an ECV map from the two T1 maps captured in the first substep 40a and the second substep 40b.

This reconstruction algorithm is applied to the captured raw data multiple times in the further method step 42. In a first substep 42a the T1 map captured in the first substep 40a before contrast medium is administered and the T1 map captured in the second substep 40b after contrast medium is administered are registered to one another by a registration unit (not shown) of the reconstruction computer 33.

A second substep 42b of the reconstruction method is performed as a function of multiple virtual values of a physiological parameter in a further method step 44 by means of a parameter provision unit (not shown) of the reconstruction unit 33. In the present case the physiological parameter is a laboratory value of the examination object, namely a hematocrit value of the examination object. Since the hematocrit value for patients is typically between 30 percent and 70 percent and is typically determined with an accuracy of approximately 1 percent, 41 different virtual hematocrit values 44-1,44-2, . . . ,44-41 are provided by the parameter provision unit. The 41 virtual hematocrit values 44-1,44-2, . . . ,44-41 are graduated in 1 percent steps from 30 percent to 70 percent. The 41 virtual hematocrit values 44-1,44-2, . . . ,44-41 are therefore: 30 percent, 31 percent, 32 percent, . . . , 70 percent. Obviously other percentage values that appear expedient to the person skilled in the art, or a differing number of percentage values, can also be provided.

The second substep 42b of the reconstruction method is accordingly performed 41 times. Each time the T1 maps coregistered in the first substep 42a are used as input values. The coregistered T1 maps are however further processed 41 times with the different virtual hematocrit values 44-1, 44-2, . . . ,44-41 provided in the further method step 44. The raw data is here further processed by means of a computational operation described below, whereby the value of the physiological parameter, the virtual hematocrit value 44-1, 44-2, . . . ,44-41, is used as a variable in the computational operation.

For example, in the second substep 42b 41 different ECV maps 42b-1,42b-2, . . . ,42b-41 are created. The respective ECV values of the ECV maps are calculated pixel by pixel from the respective T1 values before contrast medium is administered (T1$_{myo,pre}$ for myocardial tissue and T1$_{blood,pre}$ for blood tissue) and after contrast medium is administered (T1$_{myo,post}$ for myocardial tissue and T1$_{blood,post}$ for blood tissue) and from the respective hematocrit value H 44-1,44-2, . . . ,44-41, on the basis of this formula to be applied pixel by pixel:

$$ECV = (1-H) \times \frac{\left(\frac{1}{T1_{myo,post}} - \frac{1}{T1_{myo,pre}}\right)}{\left(\frac{1}{T1_{blood,post}} - \frac{1}{T1_{blood,pre}}\right)}$$

The 41 different ECV maps 42b-1,42b-2, . . . ,42b-41, which are calculated on the basis of the respective 41 different hematocrit values H 44-1,44-2, . . . ,44-41, represent 41 different medical image data records. The medical image data records thus comprise a representation of a spatially resolved distribution of an extracellular volume of the examination object.

It should be noted that the reconstruction algorithm according to FIG. 3 is particularly efficient in saving computational time, since the compute-intensive first substep 42a, the registration of the T1 maps, need only be performed once and can serve as the basis for the pixel-by-pixel application of the above formula in the second substep 42b, which is less compute-intensive but has to be performed more frequently.

In the further method step 43, namely the provision of the medical image data records, the 41 different ECV maps 42b-1,42b-2, . . . ,42b-41 are provided. In the present case the ECV maps 42b-1,42b-2, . . . ,42b-41 are displayed on the display unit 25 in the form of a series of images 43a. The provision of ECV maps 42b-1,42b-2, . . . ,42b-41 in each case comprises a provision of the hematocrit value 44-1,44-2, . . . ,44-41 associated with the ECV maps 42b-1, 42b-2, . . . ,42b-41, the value being in each case displayed together with the ECV map 42b-1,42b-2, . . . ,42b-41 in the series of images 43a.

In a further method step 47 the actual hematocrit value of the examination object is then captured after the creation of the medical image data records by means of a parameter capture unit (not shown). The laboratory value is therefore not available until after the different ECV maps 42b-1,42b-2, . . . ,42b-41 have been reconstructed. In a further method step 48 the ECV map 42b-1,42b-2, . . . ,42b-41 associated with the measured hematocrit value can then be selected from the series of images of the ECV maps 42b-1, 42b-2, . . . ,42b-41 by a user or automatically. A fresh reconstruction of the ECV maps 42b-1,42b-2, . . . ,42b-41 with the measured hematocrit value is not necessary.

Furthermore, in a method step 45 a characterization value 45-1,45-2, . . . ,45-41 is determined in each case for each ECV map 42b-1,42b-2, . . . ,42b-41. The characterization value 45-1,45-2, . . . ,45-41 is in each case determined across an image area of the ECV maps 42b-1,42b-2, . . . ,42b-41. The characterization value 45-1,45-2, . . . ,45-41 in each case characterizes an image content of the image area of the ECV maps 42b-1,42b-2, . . . ,42b-41. For example, it is conceivable for the mean value of the extracellular volume to be determined across a selected region of interest (ROI) for each ECV map 42b-1,42b-2, . . . ,42b-41.

The provision of the ECV maps 42b-1,42b-2, . . . ,42b-41 in the further method step 43 in each case is a provision of the characterization value 45-1,45-2, . . . ,45-41 associated with the ECV maps 42b-1,42b-2, . . . ,42b-41.

Furthermore, in a method step 46 a functional connection is determined by the reconstruction unit 33 between the characterization value 45-1,45-2, . . . ,45-41 and the hematocrit value 44-1,44-2, . . . ,44-41. The functional connection is then displayed on the display unit 25 in a diagram display.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for generating medical image data records of an examination object, comprising:

operating a magnetic resonance scanner, while an examination object is situated in the magnetic resonance scanner, to acquire raw magnetic resonance data from the examination object;

providing a computer with a reconstruction algorithm designed to reconstruct a medical image data record from the raw magnetic resonance data and a virtual value of a physiological parameter that has not been obtained from the examination object, said virtual value being selected from the group consisting of blood pressure, cardiac rate, oxygen saturation, temperature, and a hematocrit value;

providing said raw magnetic resonance data acquired from the examination object to said computer and, in said computer, generating at least two medical image data records by applying said reconstruction algorithm at least twice to the raw magnetic resonance data and using a different virtual value of said physiological parameter respectively in said at least two applications of said reconstruction algorithm so as to generate said at least two medical image data records; and making said at least two medical image data records available in electronic form at an output of said computer.

2. A method as claimed in claim 1 comprising making said at least two medical image data records available in said electronic form respectively associated with an electronic representation of the respective virtual value of the physiological parameter that was used to generate the respective medical image data record.

3. A method as claimed in claim 1 comprising providing said at least two medical image data records in said electronic form as a series of images.

4. A method as claimed in claim 1 comprising, after generating said at least two medical image data records, measuring an actual value of said physiological parameter from the examination object, and selecting one of said at least two medical image data records for which said actual value most closely matches said virtual value.

5. A method as claimed in claim 1 comprising operating said magnetic resonance scanner to acquire said raw magnetic resonance data as a T1 map of the examination object, and thereafter administering a contrast agent to the examination object, and thereafter operating said magnetic resonance scanner, while the examination object is situated therein, to acquire further raw magnetic resonance data as a further T1 map of the examination object with said contrast medium therein.

6. A method as claimed in claim 1 comprising providing said computer with said reconstruction algorithm configured to represent a spatially resolved distribution of an extracellular volume of the examination object.

7. A method as claimed 1 wherein said physiological value is a hematocrit value, and wherein said method comprises operating said magnetic resonance scanner to acquire said raw magnetic resonance data from the examination subject so as to include T1 data and, in said computer, calculating different extracellular volume (ECV) values and ECV maps using said T1 data and said hematocrit value.

8. A method as claimed in claim 7 comprising, in said computer, a region of interest (ROI) within each of said at least two medical image data records and calculating a mean of the ECV across each ROI, and providing said at least two image data records in said electronic form together with an electronic representation of the respective calculated mean of the ECV across each ROI in each medical image data record.

9. A medical imaging apparatus comprising:
a magnetic resonance scanner;
a control computer configured to operate said magnetic resonance scanner, while an examination object is situated in the magnetic resonance scanner, to acquire raw magnetic resonance data from the examination object;
an image reconstruction computer configured with a reconstruction algorithm designed to reconstruct a medical image data record from the raw magnetic resonance data and a virtual value of a physiological parameter that has not been obtained from the examination object, said virtual value being selected from the group consisting of blood pressure, cardiac rate, oxygen saturation, temperature, and a hematocrit value;
said image reconstruction computer being provided with said raw magnetic resonance data acquired from the examination object, and said image reconstruction computer being configured to generate at least two medical image data records by applying said reconstruction algorithm at least twice to the raw magnetic resonance data and using a different virtual value of said physiological parameter respectively in said at least two applications of said reconstruction algorithm so as to generate said at least two medical image data records; and
said image reconstruction computer being configured to make said at least two medical image data records available in electronic form at an output of said image reconstruction computer.

* * * * *